(12) United States Patent
Fetsko

(10) Patent No.: US 8,431,084 B2
(45) Date of Patent: Apr. 30, 2013

(54) CRYSTALLIZER FOR PRODUCING PHENOL-BPA ADDUCT CRYSTALS

(75) Inventor: Stephen W. Fetsko, Hingham, MA (US)

(73) Assignee: Badger Licensing LLC, Cambridge, MA (US)

( * ) Notice: Subject to any disclaimer, the term of this patent is extended or adjusted under 35 U.S.C. 154(b) by 399 days.

(21) Appl. No.: 12/821,186

(22) Filed: Jun. 23, 2010

(65) Prior Publication Data

US 2011/0319670 A1 Dec. 29, 2011
US 2012/0142974 A9 Jun. 7, 2012

(51) Int. Cl.
*B01D 9/02* (2006.01)

(52) U.S. Cl.
USPC ............ 422/245.1; 117/68; 117/70; 117/200; 117/206; 422/252; 422/253; 422/255; 422/256; 422/257; 422/258; 422/259; 422/261; 422/269; 422/273; 422/275; 422/276; 422/277; 422/278; 422/279; 422/281

(58) Field of Classification Search .................... 117/68, 117/70, 200, 206, 925; 422/245.1, 252–253, 422/255–259, 261, 269, 273, 275–279, 281
See application file for complete search history.

(56) References Cited

U.S. PATENT DOCUMENTS

| | | | | |
|---|---|---|---|---|
| 1,845,742 | A | * | 2/1932 | Cocksedge ................ 23/301 |
| 1,997,277 | A | * | 4/1935 | Burke et al. ................ 422/252 |
| 3,303,121 | A | * | 2/1967 | Torobin et al. ............. 208/37 |
| 3,364,690 | A | * | 1/1968 | Torobin .................... 62/534 |
| 3,486,848 | A | * | 12/1969 | Hendrix ................... 62/534 |
| 4,927,978 | A | | 5/1990 | Buechele et al. |

FOREIGN PATENT DOCUMENTS

| | | |
|---|---|---|
| EP | 0720976 B1 | 1/1999 |
| FR | 1341745 | 9/1963 |
| GB | 1082177 | 9/1967 |
| JP | 2004188349 A * | 7/2004 |

OTHER PUBLICATIONS

International Search Report and Written Opinion issued in a corresponding application PCT/US2011/039568 on Aug. 8, 2011.
Chemical Engineers Handbook (Perry and Chilton, 1973), 5th edition p. 1-22.

* cited by examiner

*Primary Examiner* — Michael Kornakov
*Assistant Examiner* — Kenneth A Bratland, Jr.
(74) *Attorney, Agent, or Firm* — Roberts Mlotkowski Safran & Cole, P.C.

(57) ABSTRACT

A crystallizer for the evaporative production of phenol-BPA adduct crystals is provided that achieves more uniform crystal growth while suppressing undesired crystal nucleation. The crystallizer includes a cylindrical vessel; a draft tube concentrically disposed within the cylindrical vessel such that an annular space is defined between the vessel and tube; an impeller that circulates liquid in the vessel through the draft tube and the annular space, and a plurality of nozzles mounted around an inner wall of said cylindrical vessel that introduce an evaporative coolant into the vessel. Each of the nozzles includes a discharge end disposed between about 30% and 60% of a radial extent of the annular space, and is located below an upper end of the draft tube a distance of between about 50% to 150% of the diameter of the vessel. Such a nozzle arrangement provides a consistent and uniform concentration of coolant across the surface of the boiling zone that prevents or at least reduces unwanted crystal nucleation.

19 Claims, 4 Drawing Sheets

CRYSTALLIZER FOR PRODUCING PHENOL-BPA ADDUCT CRYSTALS

FIELD

This invention generally relates to the evaporative production of phenol-BPA adduct crystals, and is particularly concerned with a crystallizer and method that achieves more uniform crystal growth while suppressing undesired crystal nucleation by means of a nozzle arrangement that more uniformly distributes evaporative coolant throughout the crystallizer vessel.

BACKGROUND

Adduct crystallization has been used for many years as a way to purify Bisphenol A. The goal of the crystallization is to produce large adduct crystals that can be easily separated from the mother liquor and washed without significant breakage. Phenol-BPA adduct crystals can be formed by way of an evaporative crystallization process wherein a volatile liquid aliphatic hydrocarbon, such as pentane or hexane, is used as a coolant, as described in U.S. Pat. No. 4,927,978. The crystallization process is implemented in a crystallizer formed from a cylindrical vessel having a draft tube concentrically disposed therein. An impeller circulates the crystallizer contents down through the interior of the draft tube and up through the annular space defined between the outside of the draft tube and the inner walls of the cylindrical vessel. A conical member may be placed below the draft tube to prevent solids from building up on the floor of the vessel and to facilitate the transition from downward to upward flow.

The aliphatic hydrocarbon coolant, as well as the main crystallizer feed and a recycle feed, are each introduced into the crystallizer through separate sets of nozzles mounted around the circumference of the vessel at different heights. The set of nozzles for the main crystallizer feed is the lowest of the three sets, being located near the bottom of the vessel. Each of the nozzles for the main crystallizer feed radially extends into the lower portion of the draft tube. The set of nozzles for the recycle feed are located above the nozzles for the main crystallizer feed, and extend into the annular space defined between the outside of the draft tube and the inner walls of the cylindrical vessel. The set of nozzles for the aliphatic hydrocarbon coolant is the highest of the three sets, being located near the middle of the vessel.

In operation, the main crystallizer feed is introduced into the bottom of the draft tube, while the recycle feed enters into the annular region in the bottom half of the crystallizer vessel. The aliphatic hydrocarbon coolant enters the crystallizer in the annular area at a height sufficient to suppress its immediate vaporization, typically near the mid-point of the vessel. The contents of the crystallizer vessel are circulated down the draft tube and up the annular area using the impeller located inside the draft tube. The aliphatic hydrocarbon coolant entrained in the vessel contents vaporizes as it approaches the liquid surface at the upper end of the vessel, creating a boiling zone which cools the surrounding liquid and precipitates phenol-BPA adduct crystals. The resulting product slurry is removed from the bottom or near the bottom of the vessel via one or more product drain openings or drain nozzles, while the vaporized aliphatic hydrocarbon coolant exits from the top of the vessel. The phenol-BPA adduct crystals are separated from the product slurry and washed, and part of the liquid component separated from the washed crystals is used for the recycle feed.

SUMMARY

While the aforementioned crystallizer designs and methods are reasonably efficient in producing phenol-BPA adduct crystals, the applicant has observed that undesired crystal growth can occur in the upper portion of the vessel within the boiling zone, termed encrustation, and create crystalline masses on the crystallizer vessel walls and surfaces of the structural components that support the draft tube. The applicant has further observed that some of these crystal masses break off of the structural components and accumulate on the vessel floor since they are too large to be removed from the vessel via the vessel drain openings. Both the crystal masses and other accumulated deposits of crystals at the bottom of the vessel must periodically be removed from the vessel by a cleaning process that necessitates stopping feed to the crystallizer vessel and dissolving the encrusted solids by heating or addition of solvent. Accordingly, there is a need for an improved crystallizer and method for producing phenol-BPA adduct crystals that obviates or at least reduces the need for such periodic vessel cleaning processes, and the production downtime that accompanies such cleaning.

The present invention stems from the applicant's observation that the undesired crystal nucleation that occurs in the upper portion of prior art crystallization vessels is exacerbated by inconsistencies and non-uniformities in the flux of coolant across the surface of the boiling zone. To solve this problem, both the crystallizer and method of the invention employ a nozzle arrangement that provides a substantially more uniform flux of coolant across the surface of the boiling zone. The resulting uniform flow minimizes the degree of local supersaturation which in turn discourages unwanted crystal growth on the surfaces of the vessel and the draft tube supports in the boiling zone. More specifically, the crystallizer of the invention comprises a cylindrical vessel; a draft tube concentrically disposed within said cylindrical vessel such that an annular space is defined between said vessel and tube; a circulator that circulates liquid in the vessel through the draft tube and the annular space, and a plurality of nozzles mounted around an inner wall of said cylindrical vessel that introduce an evaporative coolant into said vessel, wherein each nozzle includes a discharge end disposed between about 30% and 60%, and more preferably between about 30% and 50%, of a radial extent of the annular space.

The nozzles are preferably located at substantially the same height on the inner wall of the vessel. The discharge ends of the plurality of nozzles are uniformly spaced around the circumference of the annular space. The discharge ends of the plurality of nozzles extend radially into the annular space at preferably the same distance, although they may be staggered at different distances within the aforementioned 30%-60% of the radial extent. The plurality of nozzles may further be located below an upper end of the draft tube a distance of between about 50% to 150% the diameter of the vessel, and more preferably between about 100% to 150% of the vessel diameter. Finally, the total number of nozzles is preferably between 8 and 18, and more preferably between 12 and 18. Such spacing, distancing, and number of nozzles provides further insurance of a uniform flux of coolant across the surface of the boiling zone.

In the method of the invention, volatile coolant is injected through the nozzles of the crystallizer at a velocity of between about 10 and 20 m/sec, and more preferably between about 12 and 18 m/sec. The coolant may be one or more of the group consisting of an aliphatic hydrocarbon, an aliphatic carbonyl, and water as disclosed in U.S. Pat. Nos. 4,209,646; 5,723, 688, and EP 0720976B1.

DETAILED DESCRIPTION OF THE EMBODIMENTS

Figure 1:
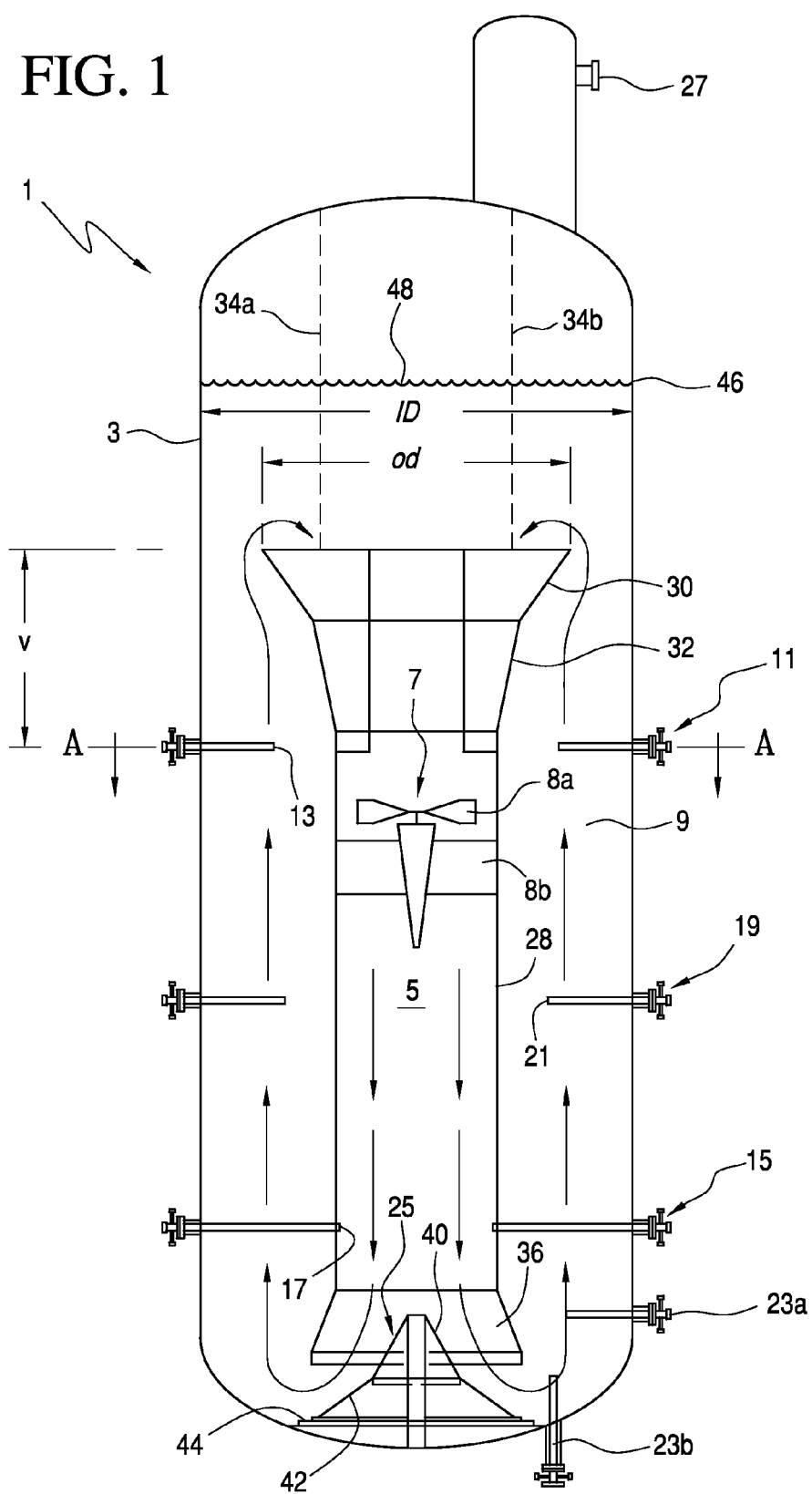
FIG. 1 is a side schematic view of the crystallizer of the invention.

With reference to FIG. 1, the crystallizer 1 of the invention generally comprises a cylindrical vessel 3, and a draft tube 5 concentrically disposed therein. The interior of the draft tube 5 includes a circulator assembly 7 having an impeller 8a positioned over a set of straightening vanes 8b. An annular space 9 is defined between the exterior of the draft tube 5 and the interior surface of the cylindrical vessel 3.

The vessel 3 of the crystallizer 1 is circumscribed by three sets of nozzles, including a ring of evaporative coolant nozzles 11, a ring of main crystallizer feed nozzles 15, and a ring of recycle feed nozzles 19.

The ring of the evaporative coolant nozzles 11 is positioned near the middle of the vessel 3. Each of the nozzles 11 is connected to a pressurized source of evaporative coolant, which is preferably a volatile liquid aliphatic hydrocarbon such as pentane or hexane, although other compounds such as aliphatic carbonyls and even water may also be used for this purpose. Each of these nozzles 11 has a discharge end 13 disposed within the annular space 9. As is described in more detail hereinafter, the height of the ring of nozzles 11 relative to the draft tube 5, the amount of radial penetration of the discharge ends 13 into the annular space 9, and number of nozzles 11 are all important if not critical aspects of the crystallizer 1.

The ring of crystallizer feed nozzles 15 circumscribes the vessel 3 near its bottom. Each of these nozzles 15 is connected to a source of pressurized crystallizer feed, which may be for example a product formed by the conventional condensation of a carbonyl compound, such as acetone, with phenol to form bisphenol A (BPA). Preferably, the bisphenol A product is distilled to remove acetone, water and excess phenol so that the main crystallizer feed stream contains about 35% bisphenol A and about 65% phenol and impurities. Each of these nozzles 15 includes a discharge end 17 disposed within the interior of the draft tube 5 so that the impeller 8a of the circulator assembly 7 immediately begins to circulate and mix the fresh crystallizer feed with the vessel contents as soon as it is introduced into the vessel 3. The ratio of circulatory flow to the total slurry outlet flow is in the range of 25:1 to 150:1, preferably between 50:1 to 100:1.

Positioned between the ring of evaporative coolant nozzles 11 and ring of feed nozzles 15 is a ring of recycle feed nozzles 19, each of which has a discharge end 21 disposed within the annular space 9. Each of the recycle feed nozzles 19 is connected to a pressurized source of recycle feed which is formed from the liquid that is centrifugally separated out of the liquid/crystal slurry product drained from the vessel 3.

Product drain nozzles 23a, 23b located near the bottom of the vessel 3 are used to drain the liquid/crystal slurry product produced inside the vessel 3 by the evaporative cooling of the crystallizer feed. A conical member 25 located on the floor of the vessel 3 promotes a circulatory flow (indicated by flow arrows) that maintains the phenol-BPA adduct crystals in suspension in the slurry, thereby discouraging the formation of unwanted crystal deposits on the floor of the vessel. A coolant vent or nozzle 27 located at the top of the vessel 3 vents evaporated coolant to cooling coils or alternately to a compressor (not shown) and then cooling coils for re-liquefaction and recycling back to the coolant nozzles 11.

Figure 2:
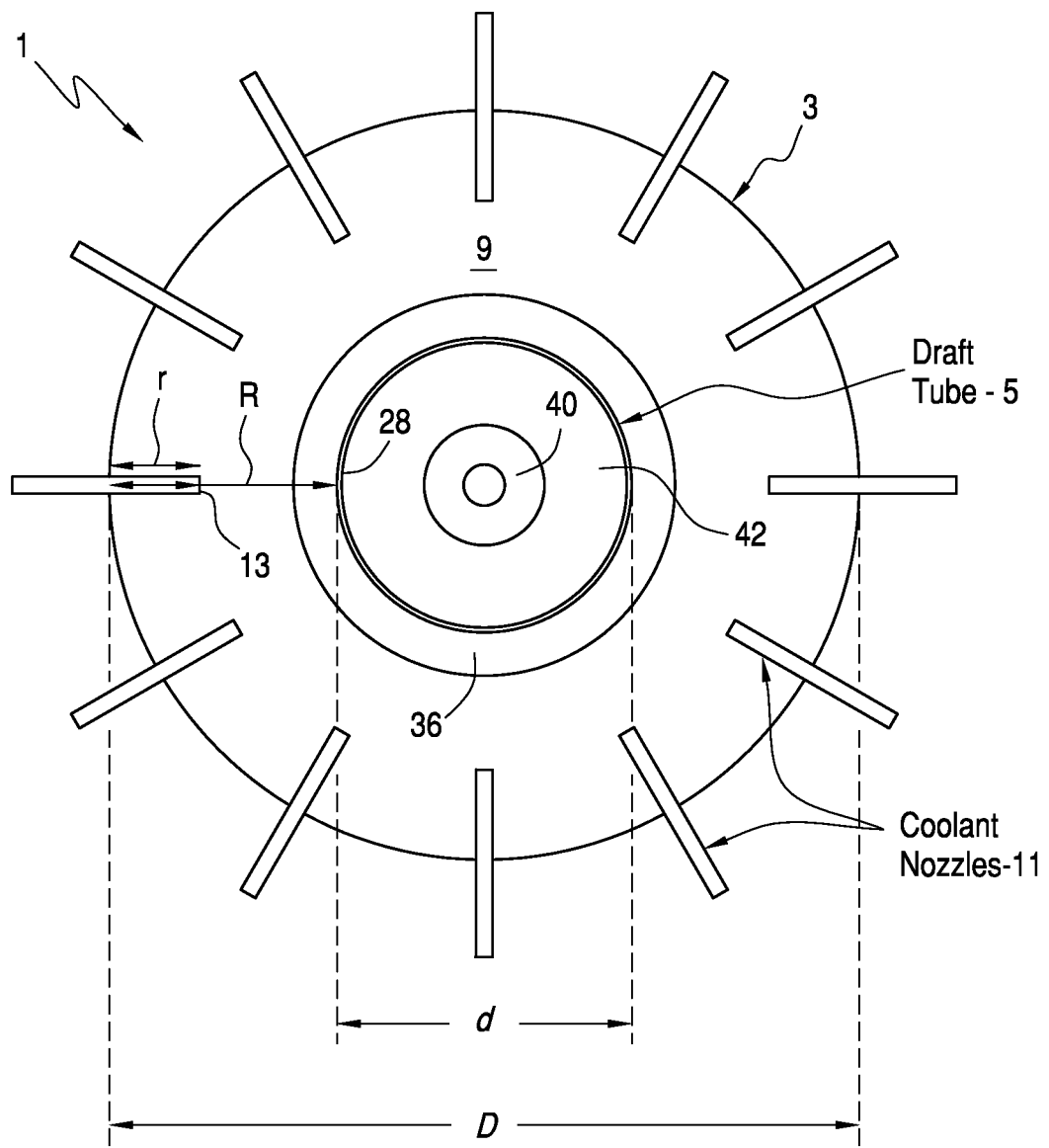
FIG. 2 is a simplified, cross sectional view of the crystallizer illustrated in FIG. 1 along the line A-A.

With reference now to FIGS. 1 and 2, the draft tube 5 has a cylindrical mid-section 28. The diameter "d" of the draft tube 5 is preferably between about 35% and 45% of the diameter "D" of the vessel 3, and most preferably 40%. The draft tube includes a top flared section 30 whose outer surface is disposed at about a 35° angle with respect to the axis of rotation of the draft tube 5. The outer diameter "od" of the top flared section 30 is preferably between about 65% and 75% of the inner diameter "ID" of the vessel 3. A transition section 32 having an outer surface disposed at about a 10° angle connects the top flared section 30 with the cylindrical mid-section 28. The provision of such a top flared section 30 and transition section 32 minimizes the entrance losses of the product slurry entering the top of the draft tube 5 and assures a uniform flow velocity profile in the annular space 9 surrounding the upper end of the tube 5. Additional flared sections can be added to the top of the draft tube to help the flow transition. The draft tube 5 is concentrically supported within the vessel 3 by a plurality of vertical support struts 34a, 34b (indicated in phantom) and radial struts (not shown).

The draft tube 5 includes a bottom flared section 36. The outer surface of the bottom flared section 36 is preferably disposed at an angle of about 20° with respect to the axis of rotation of the draft tube 5. Such flaring smoothes the transition from the downward flow of liquid/crystal slurry product from the draft tube 5 to the upward flow in the annular space 9, and prevents or at least reduces the formation of flow vortexes at the bottom of the vessel 3 where crystals can be trapped and grow to a size to where they cannot be removed through the product drains 23a, 23b. As the flare angle of section 36 increases, there is a decrease in the overall size of the flow vortexes formed. However, if the flare angle is too large, a low velocity region is created on the inside of the flared section of the draft tube. The low velocity region produces an area of inefficiency that requires higher impeller power to maintain the necessary flow. The applicant has observed that the 20° bottom flared section 36 of the draft tube 5, in combination with the conical member 25, prevents the flow velocity from falling below an inefficient rate. The conical member 25 also cooperates with the bottom flared section 36 to further ease flow direction transition, and reduce the size of vortexes formed around the bottom of the tube 5. Finally, the conical member 25 eliminates the area in the bottom section of the vessel 3 where the crystals would tend to settle and grow too large to remove.

The junction of the conical member 25 with the floor of the vessel 3 results in an area where crystals can deposit. To minimize this area, the conical member 25 is made up of three conical sections, including a top section 40 angled at about 40° from the axis of rotation of the member 25, and a middle section 42 and bottom section 44 angled at about 55° and 75°, respectively. The diameter of the base of the bottom section 44 of the conical member 25 should be between 55% and 65% of the vessel diameter. The diameter of the base of the middle section 42 should be between 45% and 55% of the vessel diameter, and the diameter of the base of the top section should be between 20% and 30% of the vessel diameter. By limiting the flare angle to 20° or below on the bottom flared section 36 and providing a conical member 25 with a triple conical section, the low flow velocity region can be eliminated and the area where crystals would tend to settle and grow can be minimized.

As previously mentioned, the crystallizer 1 of the invention prevents undesired crystal nucleation from occurring in the upper portion of the vessel 3 in the boiling zone and creating solid encrustation on the surfaces of the vessel 3, struts 34a, 34b, and other components that support the draft tube 5. The crystallizer 1 achieves this objective by arranging a selected number of coolant nozzles 11 in a novel fashion that results in a more uniform flux of coolant over the liquid surface 48 during the operation of the crystallizer 1. Specifically, as illustrated in FIG. 2, the amount of radial penetration "r" of the discharge ends 13 of the nozzles 11 into the annular space 9 is preferably adjusted to between about 30% and 60% of the annular space radial extent "R", and is more preferably adjusted to between about between about 30% and 55% of R. Additionally, as illustrated in FIG. 1, the vertical distance "V" between the ring of nozzles 11 and the upper edge of the draft tube 5 is preferably between about 50% to 150% the diameter "D" of the vessel 3, and more preferably about 100% to 150% the diameter D. Finally, the number of nozzles 11 circumscribing the vessel 3 is preferably between about 8 and 18, and is more preferably between about 12 and 18, and is most preferably 18. The applicant has found, through the following numerical simulations that these three aspects of the coolant nozzles 11 are important if not critical aspects of the crystallizer 1.

Figure 3:
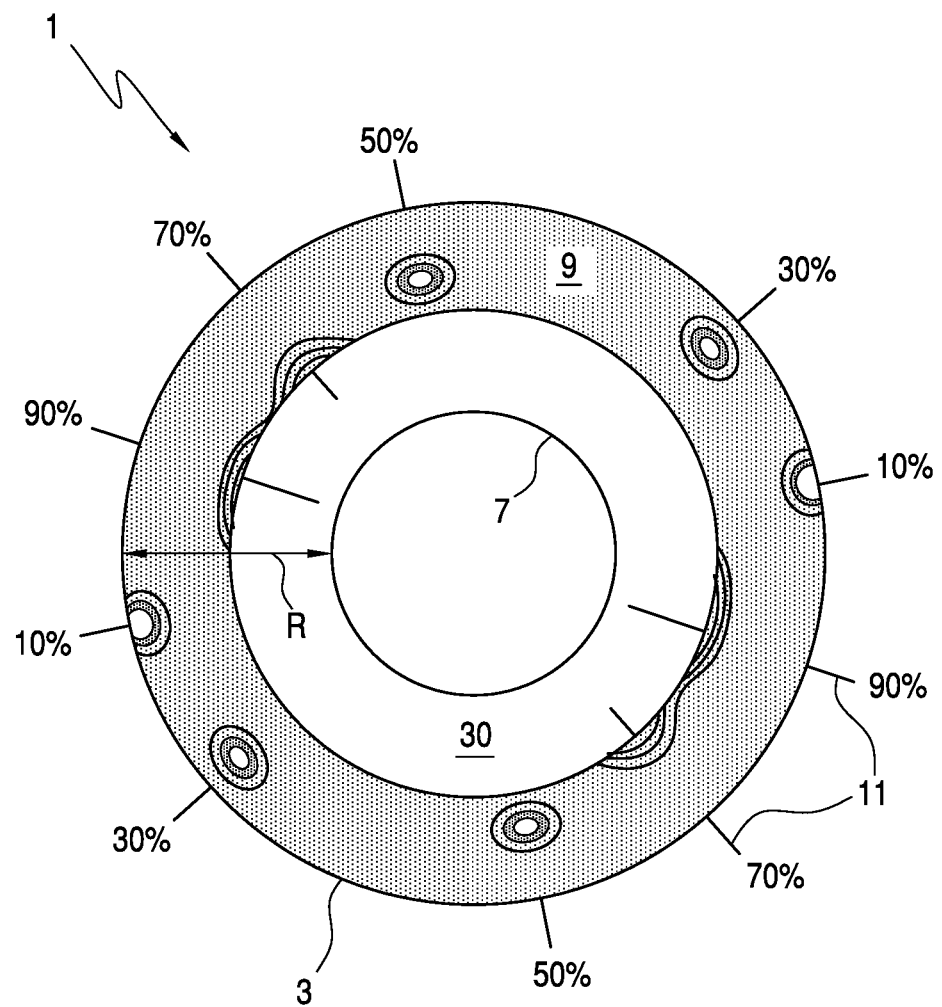
FIG. 3 illustrates the coolant volume fraction contours at the upper edge of the draft tube for coolant nozzles extending 10%, 30%, 50%, 70%, and 90% in the annular region within the crystallizer vessel.

The first simulation modeled the aliphatic hydrocarbon behavior for nozzles 11 that radially penetrated 10%, 30%, 50%, 70%, and 90% of the radial extent R of the annular region 9 measured from the crystallizer wall. FIG. 3 shows the coolant volume fraction contour at the upper edge of the of the top flared section 30 draft tube 5 within the vessel 3 for the five nozzles. The simulation was set up with five pairs of nozzles 180° apart at each percentage penetration such that the simulation included a total of ten nozzles 11, as indicated in FIG. 3. For the initial simulations, the distance between the nozzles 11 and the top of the draft tube 5 was assumed to be one-half of the vessel diameter D. The aliphatic hydrocarbon coolant velocity in the feed pipes connected to the nozzles 11 was assumed to be about 3 m/sec. The discharge ends 13 of the nozzles 11 are tapered to produce a velocity of around 15 m/sec for the coolant entering the vessel 3.

Figure 4:
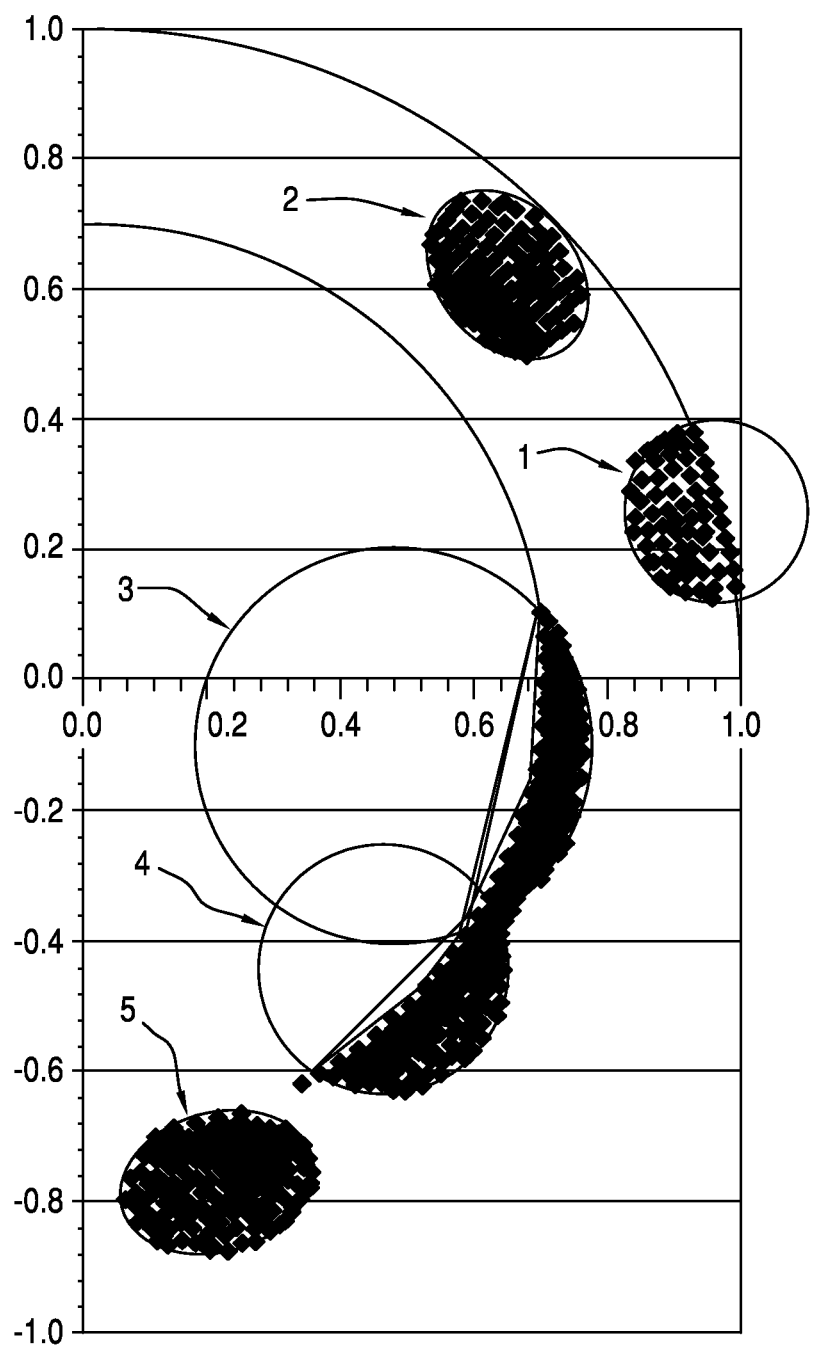
FIG. 4 is a graph of the simulated values of the coolant volume fraction at the plane at the top of the draft tube for the coolant nozzles illustrated in FIG. 3.

To calculate the covered area and percent coverage at the upper edge of the of the top flared section 30 draft tube 5, the simulation values of the coolant volume fraction in the plane at the top of the draft tube 5 greater than 1E-03 are plotted in FIG. 4. The scale of the vertical (y) axis and the horizontal (x) axis of the plot correspond to the crystallizer diameter D. The vessel wall 3 is represented by an arc drawn on the plot from the end of the positive y-axis to the end of the positive x-axis. This represents the outer diameter of the annular space 9. A second arc is drawn to represent the outer diameter of the top flared section 30 of the draft tube 5. The annular area of the plots can then be calculated using the dimensions of the concentric arcs. The origin represents the center of the draft tube.

In the plotted region there are five feed nozzles 11. If the nozzle 11 is near the center of the annular section 9 as is the case for nozzles 2 and 5 (at 30% and 50% penetration, respectively), the shape of the covered area will be a complete oval. In this case the covered area is calculated as the product of π(width/2)(height/2). If the nozzle is close to a wall as is the case with nozzle 1 (at 10% penetration) the shape of the covered area will be part of an oval. To calculate the covered area, a circle is drawn which encompasses the covered area. The area of the circle can be calculated from the diameter. A chord is then drawn to mimic the wall. On page 1-22 in the 5th edition of the Chemical Engineers Handbook (Perry and Chilton, 1973) is a table that provides the ratio of the area over the radius squared ($A/r^2$) in relation to the ratio of the chord length to the radius (chord/r). If the covered area is less than half the total circle area, then multiplying the ratio by the radius squared provides the covered area. If the covered area is greater than half the total circle area, then the result is subtracted from the total circle area to give the covered area. In some cases, as with nozzles 3 and 4 in FIG. 4 (at 90% and 70% penetration, respectively), there is still some area inside the bisected circle that is not covered. These areas can be modeled using triangles and the area of the triangles subtracted from the area above to give the covered area.

Using the plot as shown in FIG. 4, the calculated covered areas are shown in the table below. The table shows that the nozzles 11 that are closest to the center of the annular region 9 produce the greatest coverage. The results also show that when the coolant contacts either the vessel wall 3 or the wall of the draft tube 5, the covered area decreases significantly:

| Nozzle | Penetration | Area |
|---|---|---|
| 1 | 10 | 0.42 |
| 2 | 30 | 0.66 |
| 3 | 90 | 0.49 |
| 4 | 70 | 0.48 |
| 5 | 50 | 0.69 |

To determine the effect of height on the coolant coverage, simulations were run with the nozzles 11 at heights of one-half and one times the crystallizer diameter D below the top of the draft tube 5 for nozzle penetrations of 30, 40, 50 and 60 percent. The results, which are presented in the table below, showed that for both cases the greatest coverage is again found with the nozzle 11 penetrating into the center of the annular region 9. The results also showed that the coverage increases as the distance between the coolant nozzles 11 and the top of the draft tube 5 increased. The simulations showed that the coverage increased between 30 and 40 percent for the nozzles 11 with penetrations between 30 and 50 percent and increased by almost 60 percent for the nozzle 11 with 60 percent penetration.

| Penetration | Area @ Height of ½ Crystallizer Diameter | Area @ Height of 1 Crystallizer Diameter | % Increase |
|---|---|---|---|
| 30 | 0.66 | 0.86 | 30 |
| 40 | 0.64 | 0.88 | 38 |
| 50 | 0.69 | 0.98 | 30 |
| 60 | 0.52 | 0.82 | 58 |

To determine the effect of the number of nozzles 11, simulations were run with 4, 8, 12, and 18 nozzles. The total aliphatic hydrocarbon feed rate was kept the same in each simulation. For each simulation, the nozzle penetration was adjusted so that the nozzles 11 were as close to the center of the annular region 9 as possible without having the coolant contact the wall of the draft tube 5. For the simulations with 4 and 8 nozzles, this meant a penetration of 40%, while the penetration for the simulations with 12 and 18 nozzles was 50%.

The results from the four simulations are shown in the table below. The results show that the greatest total area is obtained using 18 nozzles.

| Number of Nozzles | Area per Nozzle | Total Area |
|---|---|---|
| 4 | 0.89 | 3.56 |
| 8 | 0.71 | 5.68 |
| 12 | 0.69 | 8.28 |
| 18 | 0.62 | 11.16 |

The simulation results show that the coolant is dispersed over the largest area for nozzle penetrations between 30 and 60 percent of the annulus and preferably between 30 and 50 percent. The nozzles 11 should be designed such that the coolant does not contact the draft tube 5 or the vessel wall. Lowering the elevation of the coolant injection point increases the dispersion of the coolant. The preferred elevation below the top of the draft tube 5 is between 0.5 and 1.5 times the vessel diameter D. Finally, the dispersed area increases as the number of nozzles 11 is increased. The preferred number of nozzles is between 8 and 18, and most preferably 18.

In the actual operation of the crystallizer 1, the uniform flux of coolant created by the aforementioned arrangement of coolant nozzles 11 operating at coolant flow rates between about 10 and 20 m/sec., and more preferably about 15 m/sec., evaporatively produces phenol-BPA adduct crystals in the vessel 3 while discouraging the growth of crystal masses on the structural components in the vessel 3 that support the draft tube 5, or on any other the components or surfaces of the vessel 3 in the boiling zone around the liquid surface 48. Consequently, the number of periodic cleanings of the vessel 3 is reduced substantially, thereby proportionally reducing the amount of downtime necessary to maintain efficient operation of the crystallizer.

While the invention has been described in detail with particular reference to certain preferred embodiments thereof, it will be understood that variations and modifications can be effected within the spirit and scope of the invention, which is limited only by the appended claims and equivalents thereof.

The invention claimed is:

1. A crystallizer for the formation of phenol-BPA adduct crystals by evaporative cooling, comprising
    a cylindrical vessel;
    a draft tube concentrically disposed within said cylindrical vessel such that an annular space is defined between said vessel and tube;
    a circulator that circulates liquid in the vessel through the draft tube and the annular space, and
    a plurality of nozzles mounted around an inner wall of said cylindrical vessel that introduce an evaporative coolant into said vessel, wherein each nozzle includes a discharge end disposed between 30% and 60% of a radial extent of said annular space.

2. The crystallizer defined in claim 1, wherein said nozzles are located at substantially a same height on the inner wall of the vessel.

3. The crystallizer defined in claim 1, wherein the discharge ends of said plurality of nozzles are uniformly spaced around the circumference of the annular space.

4. The crystallizer defined in claim 1, wherein the discharge ends of said plurality of nozzles are aligned radially with respect to the annular space.

5. The crystallizer defined in claim 2, wherein the plurality of nozzles is located below an upper end of the draft tube a distance of between 50% to 150% the diameter of said vessel.

6. The crystallizer defined in claim 5, wherein the plurality of nozzles is located below an upper end of the draft tube a distance of about the diameter of said vessel.

7. The crystallizer defined in claim 2, wherein the total number of nozzles is at least 12.

8. The crystallizer defined in claim 2, wherein the total number of nozzles is between 8 and 18.

9. The crystallizer defined in claim 1, wherein said circulator includes an impeller located in said draft tube.

10. The crystallizer defined in claim 1, further comprising a conical member located on a floor of said vessel in alignment with said draft tube.

11. A crystallizer for the formation of phenol-BPA adduct crystals by evaporative cooling, comprising
    a cylindrical vessel;
    a draft tube concentrically disposed within said cylindrical vessel such that an annular space is defined between said vessel and tube;
    a circulator that circulates liquid in the vessel through the draft tube and the annular space, and
    a plurality of nozzles mounted around an inner wall of said cylindrical vessel that introduce an evaporative coolant into said vessel, each of which includes a discharge end disposed between 30% and 60% of a radial extent of said annular space,
    wherein the plurality of nozzles is located below an upper end of the draft tube a distance of between 50% to 150% the diameter of said vessel.

12. The crystallizer defined in claim 11, wherein the total number of nozzles is between 8 and 18.

13. The crystallizer defined in claim 11, wherein said draft tube has a diameter of between 35% to 45% of the cylindrical vessel.

14. The crystallizer defined in claim 11, wherein said draft tube is flared at its top and bottom end.

15. The crystallizer defined in claim 14, wherein the top end of said draft tube is flared at an angle of 35° or less relative to an axis of rotation of said tube, and said bottom end is flared at an angle of 20° or less.

16. The crystallizer defined in claim 11, further comprising an impeller located in said draft tube, and a conical member located on a floor of said vessel in alignment with said draft tube.

17. The crystallizer defined in claim 16, wherein a base of said conical member is between 55% and 65% of the diameter of said vessel.

18. The crystallizer defined in claim 11, further comprising a plurality of nozzles mounted in the vessel that introduce a BPA-rich hydrocarbon feed into the vessel, and at least one opening in the vessel that discharges a slurry of phenol-BPA adduct crystals.

19. The crystallizer defined in claim 18, further comprising a plurality of nozzles mounted in the vessel that discharge a recycled hydrocarbon feed.

* * * * *